(12) United States Patent
Morrow et al.

(10) Patent No.: US 9,220,922 B2
(45) Date of Patent: Dec. 29, 2015

(54) CLEARANCE CHECK DEVICES, SYSTEMS, AND METHODS

(71) Applicant: Scott & White Healthcare, Temple, TX (US)

(72) Inventors: Andrew Morrow, Temple, TX (US); Brian Massingill, Belton, TX (US)

(73) Assignee: Scott & White Healthcare (SWH), Temple, TX (US)

( * ) Notice: Subject to any disclaimer, the term of this patent is extended or adjusted under 35 U.S.C. 154(b) by 0 days.

(21) Appl. No.: 14/559,717

(22) Filed: Dec. 3, 2014

(65) Prior Publication Data

US 2015/0159999 A1    Jun. 11, 2015

Related U.S. Application Data

(60) Provisional application No. 61/911,229, filed on Dec. 3, 2013.

(51) Int. Cl.
| | |
|---|---|
| *A61N 5/01* | (2006.01) |
| *A61N 5/10* | (2006.01) |
| *A61B 6/08* | (2006.01) |
| *A61B 6/10* | (2006.01) |
| *A61B 6/04* | (2006.01) |

(52) U.S. Cl.
CPC .............. *A61N 5/1049* (2013.01); *A61B 6/08* (2013.01); *A61B 6/102* (2013.01); *A61B 6/0492* (2013.01)

(58) Field of Classification Search
CPC . A61N 5/1048; A61N 5/1049; A61N 5/1057; A61B 6/102
See application file for complete search history.

(56) References Cited

U.S. PATENT DOCUMENTS

| | | | |
|---|---|---|---|
| 5,281,232 A | 1/1994 | Hamilton et al. | 606/130 |
| 5,822,396 A | 10/1998 | Navab et al. | 378/207 |
| 7,696,499 B2 | 4/2010 | Miller et al. | 250/493.1 |
| 7,857,512 B2 | 12/2010 | Camus | 378/196 |
| 8,093,569 B2 | 1/2012 | Miller et al. | 250/492.3 |
| 2002/0196906 A1 | 12/2002 | Mun et al. | 378/206 |
| 2008/0279333 A1* | 11/2008 | Sattler et al. | 378/98.2 |
| 2009/0003522 A1* | 1/2009 | Chien et al. | 378/65 |
| 2009/0308400 A1 | 12/2009 | Wilson et al. | 128/845 |
| 2011/0006230 A1* | 1/2011 | Fadler | 250/522.1 |
| 2011/0036356 A1 | 2/2011 | Arn et al. | 128/845 |

(Continued)

OTHER PUBLICATIONS

Brahme, et al. "4D laser camera for accurate patient positioning, collision avoidance, image fusion and adaptive approaches during diagnostic and therapeutic procedures," Medical Physics 35, 1670 (2008); doi: 10.1118/1.2889720.

(Continued)

*Primary Examiner* — Jack Berman
*Assistant Examiner* — Eliza Osenbaugh-Stewar
(74) *Attorney, Agent, or Firm* — Norton Rose Fulbright US LLP

(57) ABSTRACT

Clearance check devices, systems, and methods that can be used to indicate whether a proposed treatment plan will cause a collision between a patient/couch and a medical device, such as a linac, are described herein. Some devices and/or systems include an adjustable clearance member to account for the rotation of the medical device and a rotatable frame segment to account for the rotation of the patient or couch. Others include a frame segment that has an inner surface defining an arc that has a radius that is substantially equal to or less than an orbital radius of a centermost portion of a medical equipment component. Still others are disclosed.

20 Claims, 13 Drawing Sheets

(56) References Cited

U.S. PATENT DOCUMENTS

2011/0226260 A1  9/2011  Eder et al. ............... 600/410
2012/0027167 A1  2/2012  O'Brien et al. ........... 378/208

OTHER PUBLICATIONS

Furhang, et al. "Clearance assurance for stereotactic radiosurgery and radiotherapy" Medical Physics 29, 45 (2202); doi: 10.1118/1.1429240.

Hua, et al. "A practical approach to prevent gantry-couch collision for linac-based radiosurgery," Medical Physics 31, 2128 (2004); doi: 10.1118/1.1764391.

Muthuswamy and Lam "A method of beam-couch intersection detection," Medical Physics 26, 229 (1999); doi: 10.1118/1.598509.

Pallotta, et al. "A phantom evaluation of Sentinel™, a commercial laser/camera surface imaging system for patient setup verification in radiotherapy," Medical Physics 39, 706 (2012); doi: 10.1118/1.3675973.

Tsiakalos, et al. "Graphical treatment simulation and automated collision detection for conformal and stereotactic radiotherapy treatment planning," Medical Physics 28, 1359 (2001); doi: 10.1118/1.1381552.

Zou, et al. "A clinically feasible method for the detection of potential collision in proton therapy," Medical Physics 39, 7094 (2012); doi: 10.1118/1.4760988.

* cited by examiner

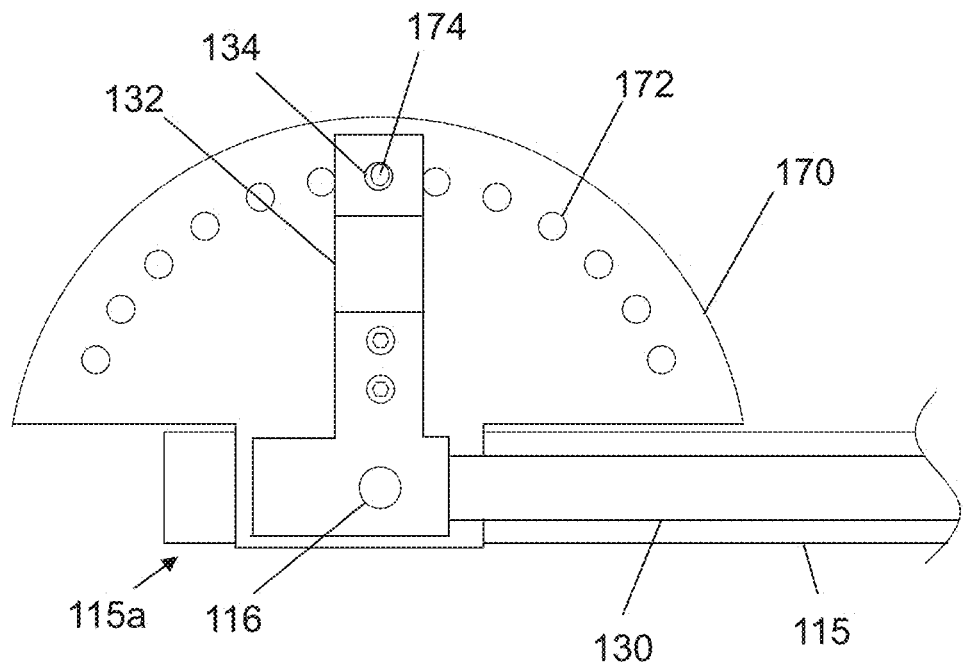
FIG. 2C(i)
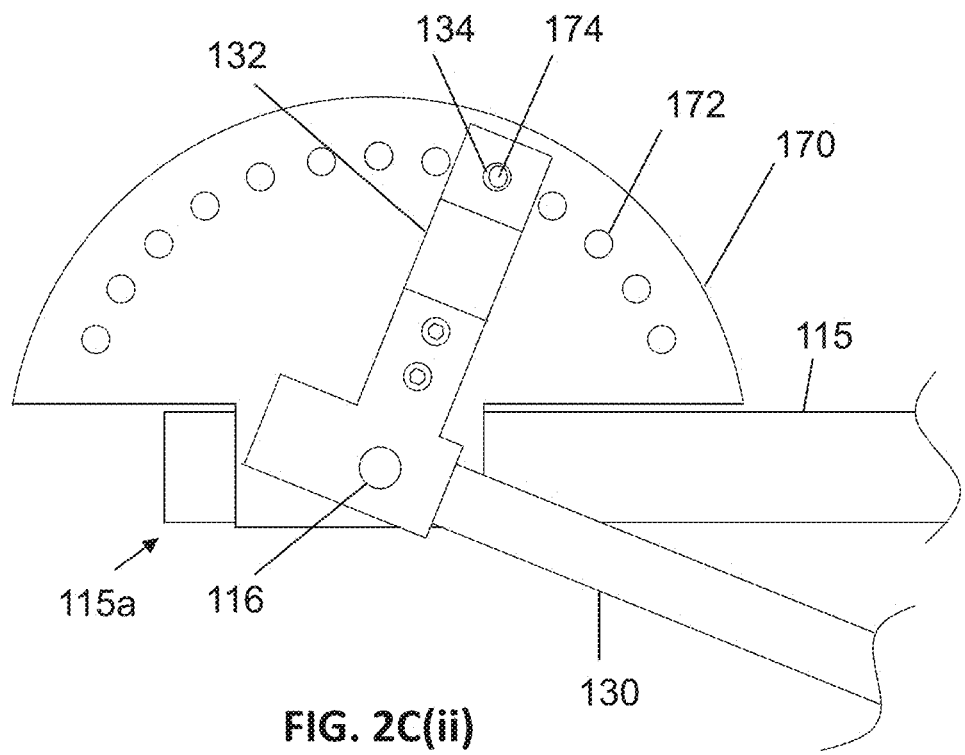
FIG. 2C(ii)

CLEARANCE CHECK DEVICES, SYSTEMS, AND METHODS

CROSS REFERENCE TO RELATED APPLICATIONS

This application is a Non-Provisional of U.S. Provisional Application No. 61/911,229 filed Dec. 3, 2013. The entire text of the above-referenced disclosure is specifically incorporated herein by reference.

BACKGROUND

A. Field of the Invention

The invention generally concerns devices, systems, and methods to predict collisions between an object and a device, part of which is configured to orbit at least partially around the object.

B. Description of Related Art

Medical devices that have a moving gantry, such as a linear accelerator (hereinafter "linac"), are found in the field of radiation therapy, with the therapy source being arranged on the gantry. Such medical devices often have projecting parts (e.g., a treatment head/collimator) that can orbit around a patient in order, for example, to direct the therapy beam onto the patient from different directions. In addition to the movement of the gantry, the patient and couch can also be rotated or laterally moved during treatment. Moving the radiation source and the patient during a treatment can improve radiation dose distributions to a treatment target, as measured by better coverage of the treatment target and the reduced impact on surrounding normal tissue.

However, if one is not careful, these coordinated movements can result in couch-gantry collisions and/or patient-gantry collisions. Undetected potential or actual collisions between the patient/couch and the gantry can be a risk to patient safety, delay the start of the treatment, and reduce clinical efficiency, especially when these collisions are not realized until the treatment plan is finished and the fields are checked on the machine, or even later, when the patient is already on the couch. As such, gantry collisions are a prominent concern for treatment planning when these types of medical devices are used.

Several recent solutions for predicting gantry collisions are software based and use geometric calculations to create a virtual collision detection system. These programs are difficult to implement or can be awkward or cumbersome for routine use in an average clinic.

SUMMARY

Embodiments of the present disclosure relate to devices, systems, and methods to predict collisions between an object and a device, at least part of which is configured to orbit at least partially around the object. Such orbiting devices can include a portion of a linac.

One aspect of this disclosure relates to a clearance check device having: an upright support and a frame segment couplable to the upright support, the frame segment having a surface defining an arc that has a radius that, when the frame segment is coupled to the upright support, is substantially equal to or less than an orbital radius of a centermost portion of a medical device component moveable along an orbital path during radiation delivery. Another aspect of this disclosure relates to a clearance check device comprising: an upright support; a frame segment having an inner surface and an outer surface; and a first attachment feature configured to couple the frame segment to the upright support, a section of the outer surface facing the upright support and the inner surface defining an arc that has a radius that is substantially equal to or less than an orbital radius of a portion (e.g., a centermost portion) of a medical device component moveable along an orbital path such that, during use, contact between the frame segment and an object indicates a potential collision between the object and the medical device component.

Embodiments described above may further comprise at least two alignment targets to facilitate alignment of the device. During use, at least one alignment target may be positioned so as to align with a sagittal laser and at least one other alignment target may be positioned to align with a coronal laser. Moreover, various embodiments may be configured such that the frame segment can be repositioned along the orbital path or be at two different positions along the orbital path at two different times. In addition, in the same or different embodiments, the vertical position of the frame segment can be vertically adjusted, by either adjusting the position of the frame segment relative to the upright support or adjusting the height of the upright support. In various embodiments, the frame segment is an arced frame segment, or alternatively, an annular frame comprises the frame segment.

Yet another aspect of this disclosure relates to a clearance check device configured to check for a potential collision between an object and a medical device component represented by the clearance check device and capable of orbiting at least partially about the object at a later time, the clearance check device comprising: an upright support; a horizontal support couplable to or integral with and extending from the upright support; a clearance member mount, such as a frame segment, couplable to the horizontal support so as to rotate about a vertical axis that passes through the horizontal support; and a clearance member couplable to the clearance member mount. A further embodiment of the above device relates to the clearance member configured to be repositionable along the length of the frame segment. In other aspects of the disclosure, a clearance check device comprises an upright support; a horizontal support coupled to and extending from the vertical support; a frame segment coupled to and extending downward or upward from the horizontal support; a first attachment feature configured to rotatably couple the frame segment to the horizontal support, the frame segment having a vertical axis of rotation that passes through the first attachment feature; a clearance member; and a second attachment feature configured to couple the clearance member to the frame segment, where, during use, contact between the clearance member and an object indicates a potential collision between the object and a medical device component intended to orbit at least partially about the object at a later time. A further embodiment of the above device relates to the clearance member configured to be repositionable along the length of the frame segment.

The embodiments described above may further comprise at least two alignment targets to facilitate alignment of the device. During use, at least one alignment target may be positioned so as to align with a sagittal laser and at least one other alignment target may be positioned to align with a coronal laser. Moreover, various embodiments may be configured such that the frame segment can be repositioned along the orbital path or be at two different positions along the orbital path at two different times. In addition, in the same or different embodiments, the vertical position of the frame segment can be vertically adjusted, by either adjusting the position of the frame segment relative to the upright support or adjusting the height of the upright support. In various embodiments, the upright support is supported by a base or is attachable to a table upon which the object is positioned.

Another aspect of the disclosure relates to kits comprising a clearance check device and at least two frame segments that can be interchanged. Similarly, another aspect of the disclosure relates to a frame segment and/or clearance member that are dimensioned for a certain medical device and are configured to couple to an upright support previously purchased.

Aspects of the disclosure also relate to a clearance check method comprising: positioning a patient on a table; positioning a clearance check device comprising a frame segment adjacent the patient so that the frame segment substantially aligns with a transverse plane that passes through a treatment target in or on the patient; and testing for contact between the clearance check device and at least one of the patient and the table. In various embodiments, two in-room lasers can be used to align the patient and then be used to align the device. The frame segment can be rotated about a vertical axis to indicate the couch angle at which a gantry could collide with the patient or the table. Similarly, the clearance member can be repositioned along the length of the frame segment to indicate the gantry angle at which the gantry could collide with the patient or the table. In the same or different embodiments, the patient and the table can be translated along a horizontal axis of the table to test for contact with the frame segment.

The term "collision-free" is defined as being free of collisions or having a low likelihood of collisions.

The term "couch" is defined as a long seat or table upon which an object, such as a patient, can lie, sit, or be otherwise positioned when receiving a treatment or being examined or tested.

The term "isocenter" is defined as the approximate center about which a medical device component will orbit. In various embodiments, at least two in-room set-up lasers can be arranged to intersect to simulate an isocenter. In the context of linacs, the isocenter can represent the approximate intersection of the gantry's orbital axis, the couch's axis of rotation, and the collimator's axis of rotation.

The term "orbital path" is defined as a path around an object or a section of a path around the object. In some embodiments, the orbital path defines at least a segment of a circle, ellipse, or oval. In other embodiments, the orbital path defines at least a segment of a square or triangle.

The term "patient" is defined as a subject on which clearance testing can be performed. While not required, the patient can be one that receives or will receive a medical treatment or a diagnostic procedure.

The term "treatment target" is defined as a point or region on or within a patient that is targeted for purposes of treatment or testing. The point or region can be an anatomical feature, such as a tumor or lesion, on a patient.

The term "coupled" is defined as connected, although not necessarily directly, and not necessarily mechanically. Two items are "couplable" if they can be coupled to each other, and, when coupled, may still be characterized as "couplable." Unless the context explicitly requires otherwise, items that are couplable are also decouplable, and vice-versa. One non-limiting way in which a first structure is couplable to a second structure is for the first structure to be configured to be coupled (or configured to be couplable) to the second structure.

The terms "a" and "an" are defined as one or more unless this disclosure explicitly requires otherwise.

The terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, any of the present devices, systems, and methods that "comprises," "has," "includes" or "contains" one or more elements possesses those one or more elements, but is not limited to possessing only those one or more elements. Likewise, an element of a device, system, or method that "comprises," "has," "includes" or "contains" one or more features possesses those one or more features, but is not limited to possessing only those one or more features. Additionally, terms such as "first" and "second" are used only to differentiate structures or features, and not to limit the different structures or features to a particular order.

Furthermore, a structure that is capable performing a function or that is configured in a certain way is capable or configured in at least that way, but may also be capable or configured in ways that are not listed. Metric units may be derived from the English units provided by applying a conversion and rounding to the nearest millimeter.

The feature or features of one embodiment may be applied to other embodiments, even though not described or illustrated, unless expressly prohibited by this disclosure or the nature of the embodiments.

Any of the present devices, systems, and methods can consist of or consist essentially of—rather than comprise/include/contain/have—any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure may not be labeled in every figure in which that structure appears. Identical reference numbers do not necessarily indicate an identical structure. Rather, the same reference number may be used to indicate a similar feature or a feature with similar functionality, as may non-identical reference numbers.

FIGS. 2C(i) to 2C(ii) illustrate a close-up bottom view of a frame segment at the site where it is rotatably coupled to the horizontal support. FIG. 2C(i) illustrates frame segment 130 at the 0° position corresponding to a 0° couch angle, and FIG. 2C(ii) illustrates frame segment 130 at about the 15° position corresponding to about the 15° couch angle.

Figure 3A:
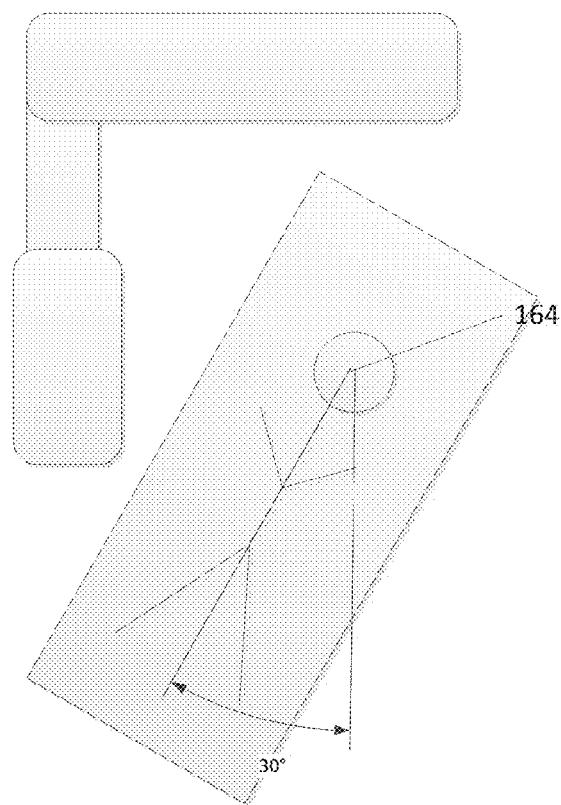
Figure 3B:
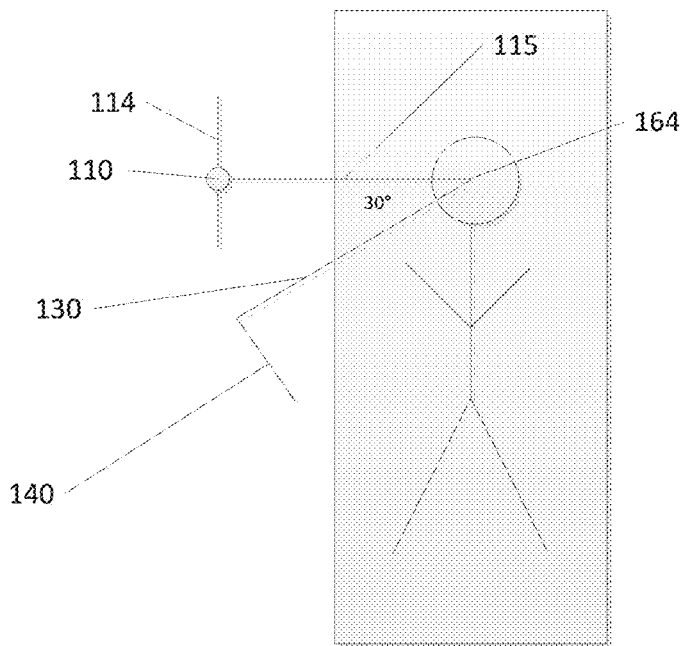

FIG. 3A illustrates a schematic top view of a patient lying on a couch at a 30° angle with a gantry rotated to a 90° angle, and FIG. 3B illustrates a schematic top view of a patient lying on a couch where a clearance member is at the 90° position on a frame segment and the frame segment is rotated 30° relative to the horizontal support to simulate the relative positions shown in FIG. 3A.

Figure 3C:
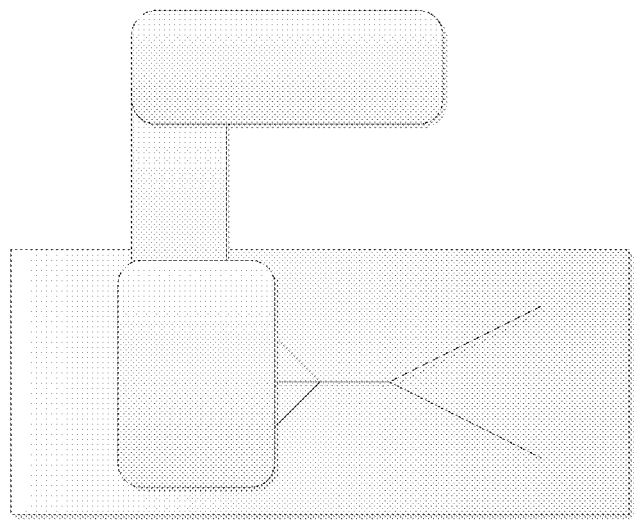
Figure 3D:
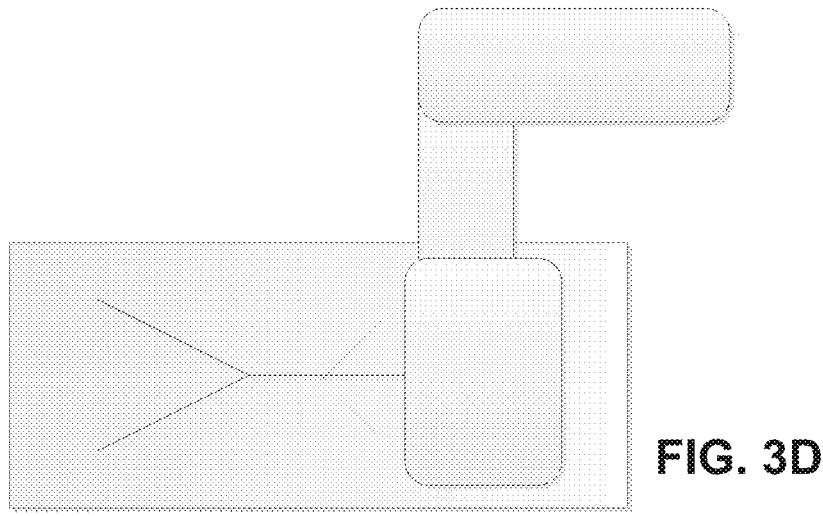

FIG. 3C illustrates a schematic top view of a patient lying on a couch at a 90° angle with a gantry rotated and located above the patient. Similarly, FIG. 3D illustrates a schematic top view of a patient lying on a couch at a 270° angle with a gantry rotated and located above the patient.

Figure 4:
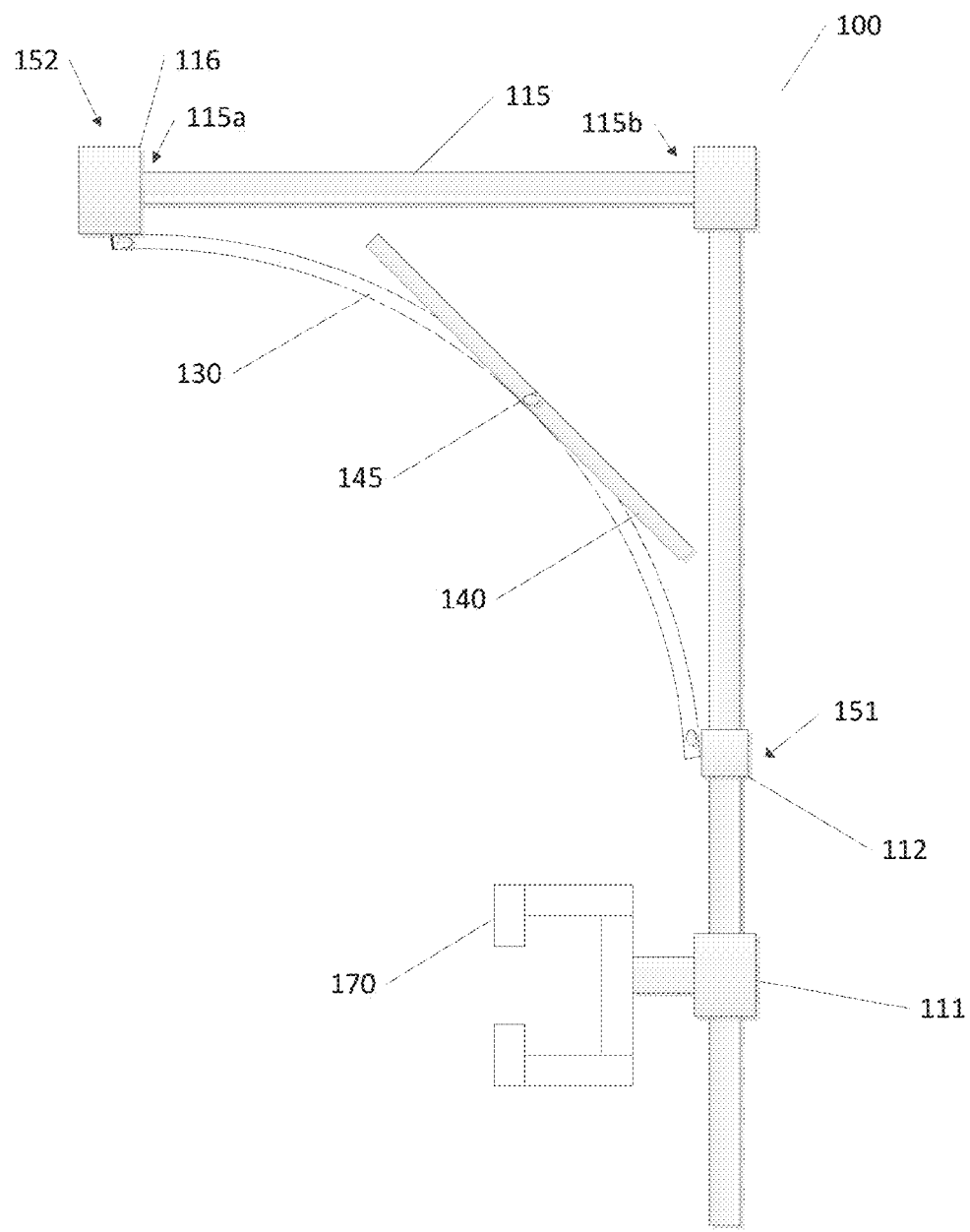

FIG. 4 illustrates a schematic side view of an embodiment with a clamp for mounting to a couch.

Figure 5:
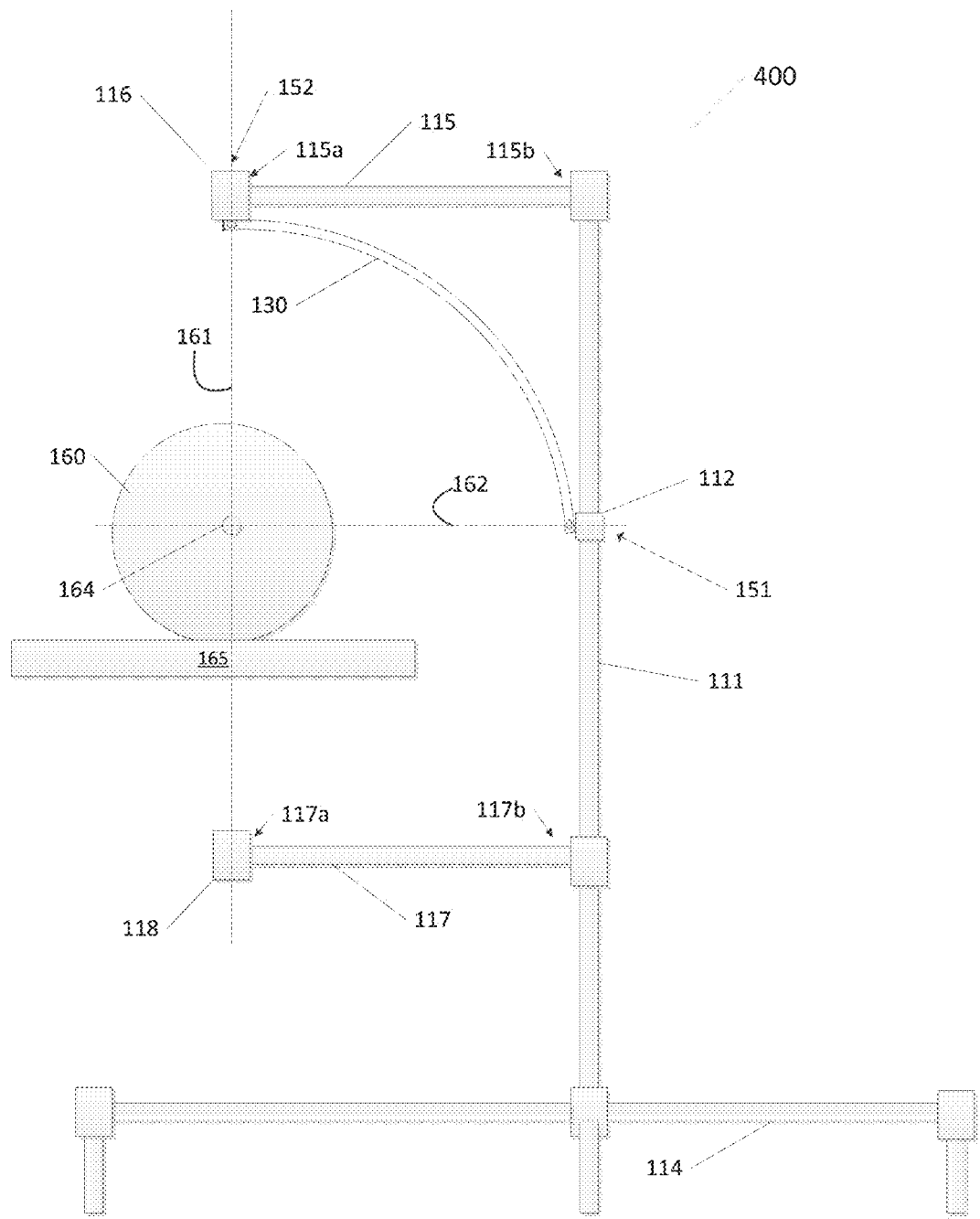

FIG. 5 illustrates a schematic side view of an embodiment with a frame segment operable as a clearance member.

Figure 6:
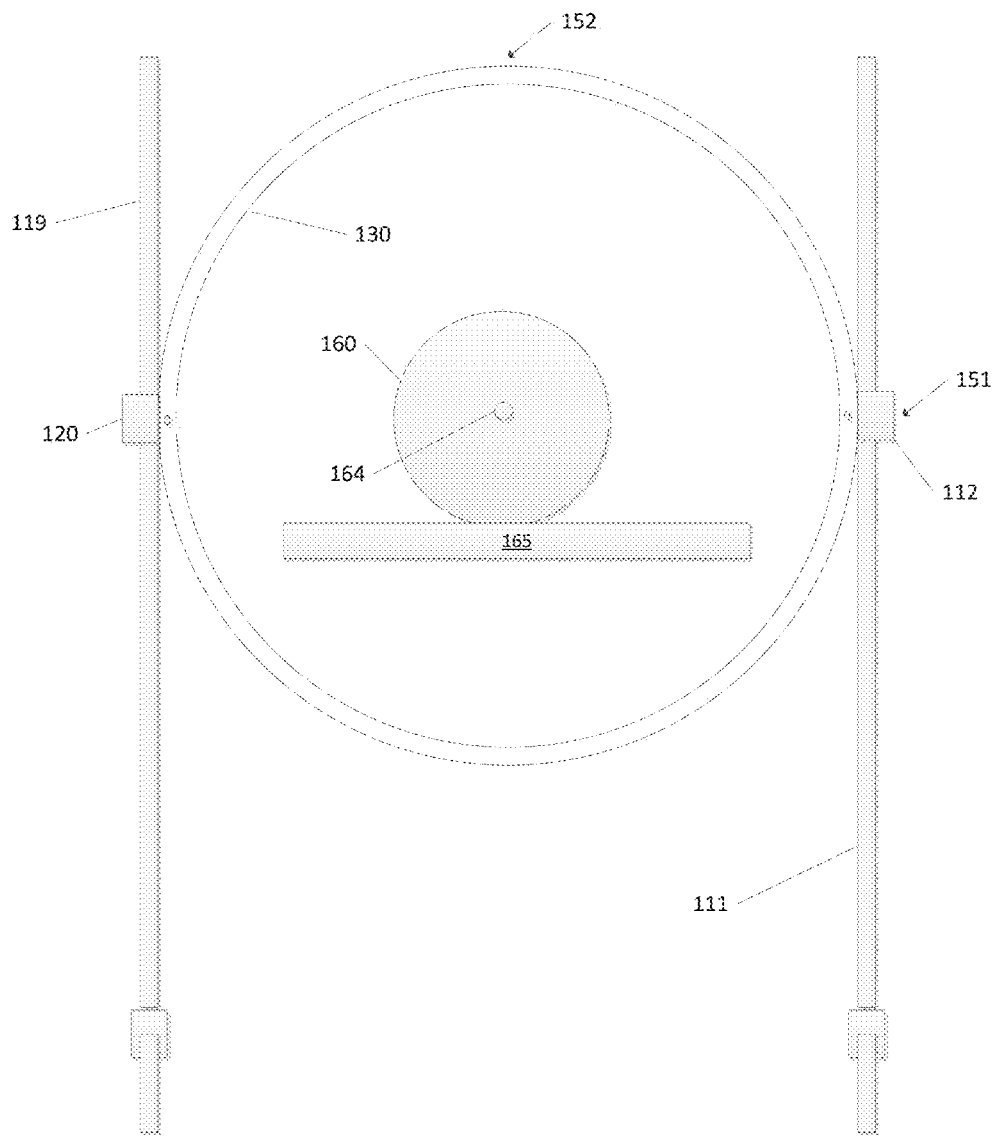

FIG. 6 illustrates a schematic side view of an embodiment with an annular frame.

DETAILED DESCRIPTION

Figure 2A:
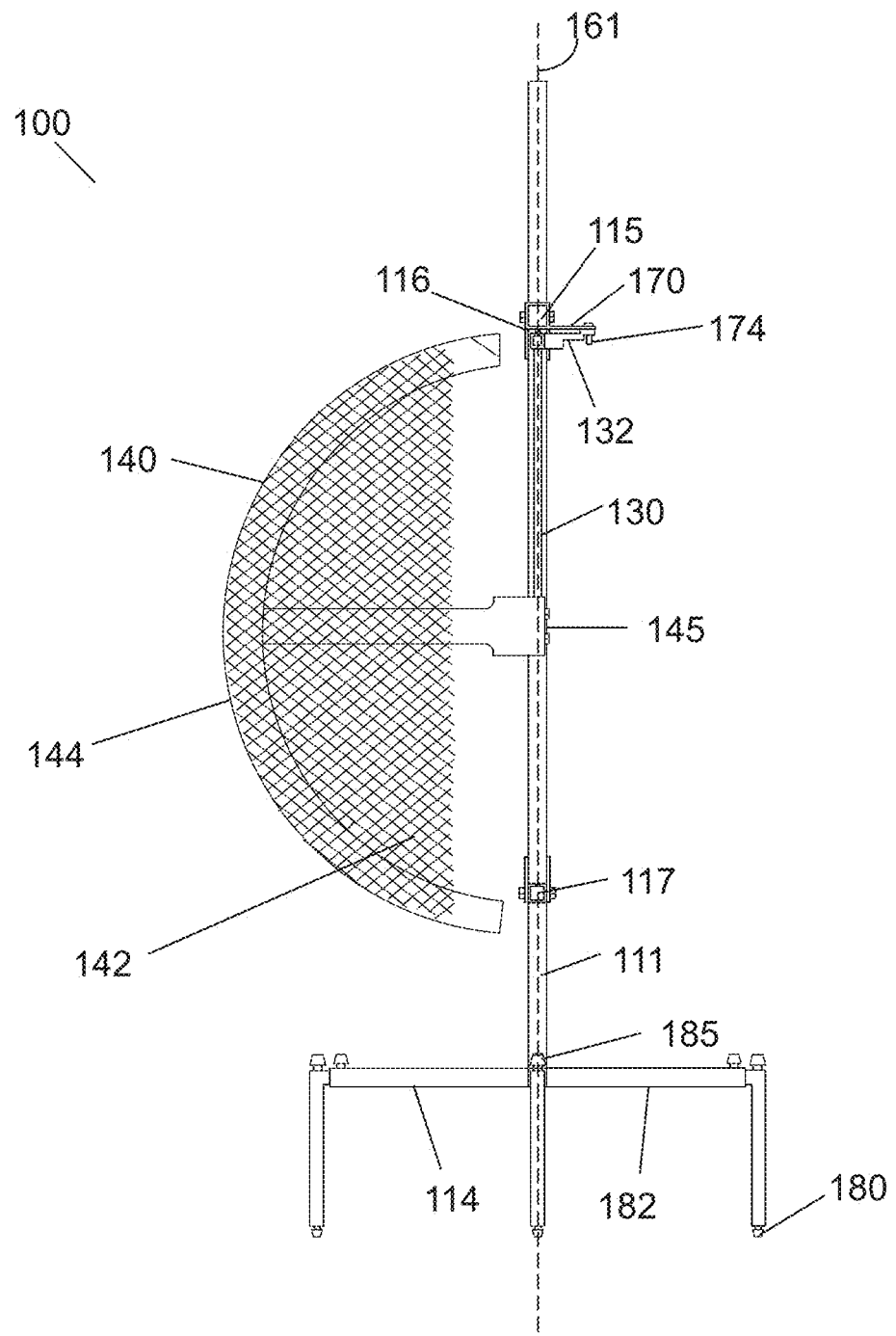
FIGS. 2A to 2B illustrate a side and front view, respectively, of an embodiment with a frame segment and a clearance member coupled thereto. The clearance member is at a 90° angle corresponding to a 90° gantry angle.
Figure 2B:
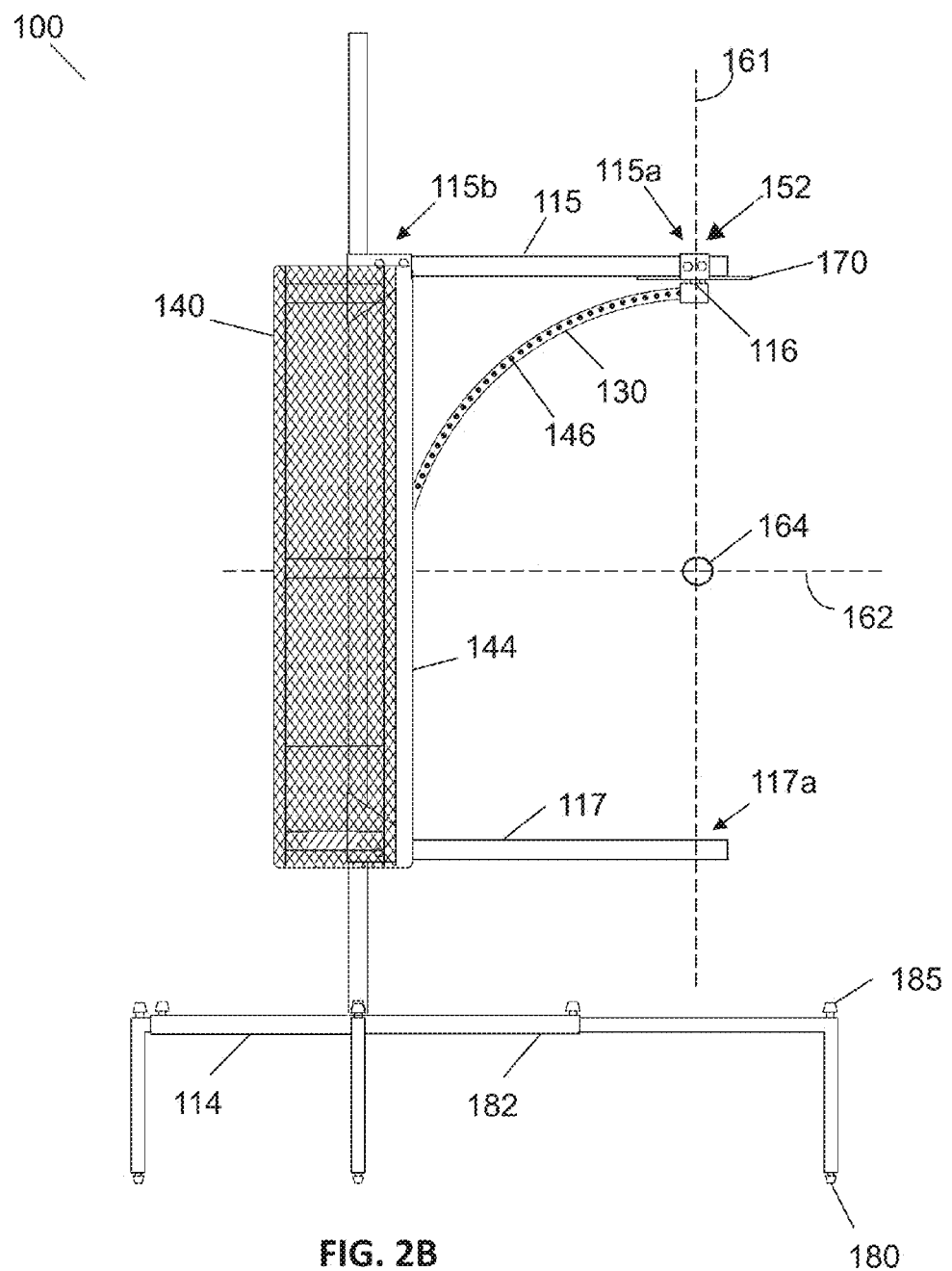

FIGS. 1A-1D depict clearance check device 100, one embodiment of the present clearance check devices that comprises an upright support 111, a horizontal support 115 coupled to and extending from upright support 111, a clearance member mount, such as a frame segment 130, being rotatably coupled to horizontal support 115, and a clearance member 140 couplable (e.g., attachable) to frame segment 130 (clearance member 140 projecting out of the page). FIGS. 2A-2B depict clearance check device 100, another embodiment of the present clearance check devices that also comprises upright support 111, horizontal support 115 coupled to and extending from upright support 111, a clearance member mount, such as frame segment 130, being rotatably coupled to horizontal support 115, and a clearance member 140 couplable (e.g., attachable) to frame segment 130. Frame segment 130 is selectively rotatable about a substantially vertical axis 161 that passes through isocenter 164 and/or attachment feature 116; frame segment 130 may also be (and in this embodiment is) configured to be securely set at a chosen angle.

When properly aligned next to an object (such as patient 160 and/or couch 165), clearance member 140 can be used to simulate a treatment plan or a portion thereof to indicate potential collisions between a component of a medical device and object 160/165. The simulated, or represented, component is intended to orbit about object 160/165 at a later time and, optionally, at a different location. As such, frame segment 130 is dimensioned so that it generally corresponds to a portion of the orbital path of the represented component, and clearance member 140 can serve as a spatial reference for the represented component. For example, the orbiting medical device component can be the treatment head or collimator of a linac, the object 160/165 can be a patient 160 lying on a couch 165, and, during use, contact between clearance member 140 and patient 160 indicates a potential collision between patient 160 and the treatment head. By using clearance check device 100, the actual medical device is not needed to determine whether or where there could be a collision between patient 160 and the medical device component. Therefore, to the extent required, the boundaries of collision-free use of the medical device can be defined in advance of a treatment procedure, increasing the time that the medical device can be utilized for actual treatment and improve the efficiency of the planning process.

Figure 1A:
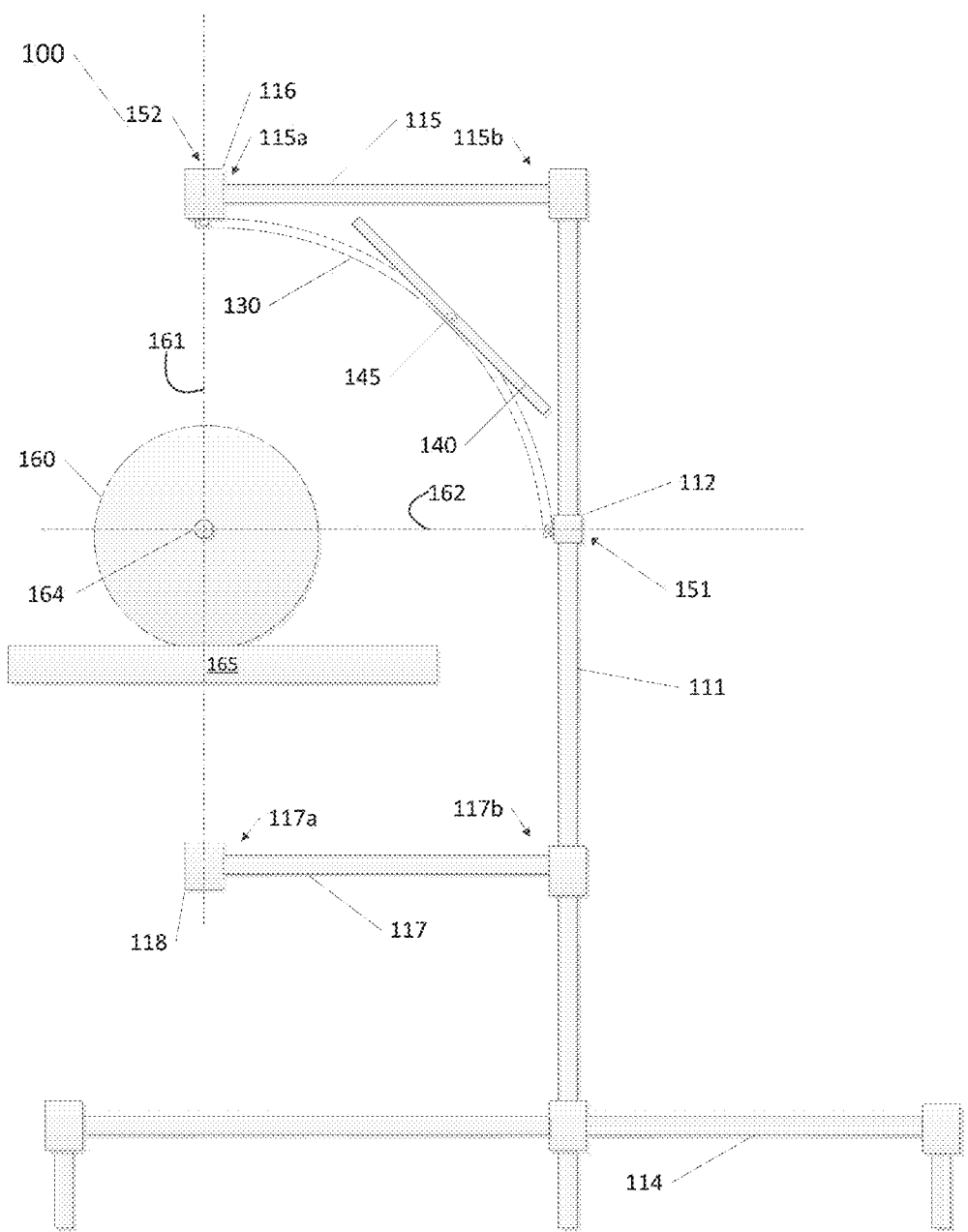
FIGS. 1A to 1D illustrate a schematic side view of an embodiment with a frame segment and a clearance member coupled thereto, wherein the frame segment is located on different sections of an orbital path.
Figure 1B:
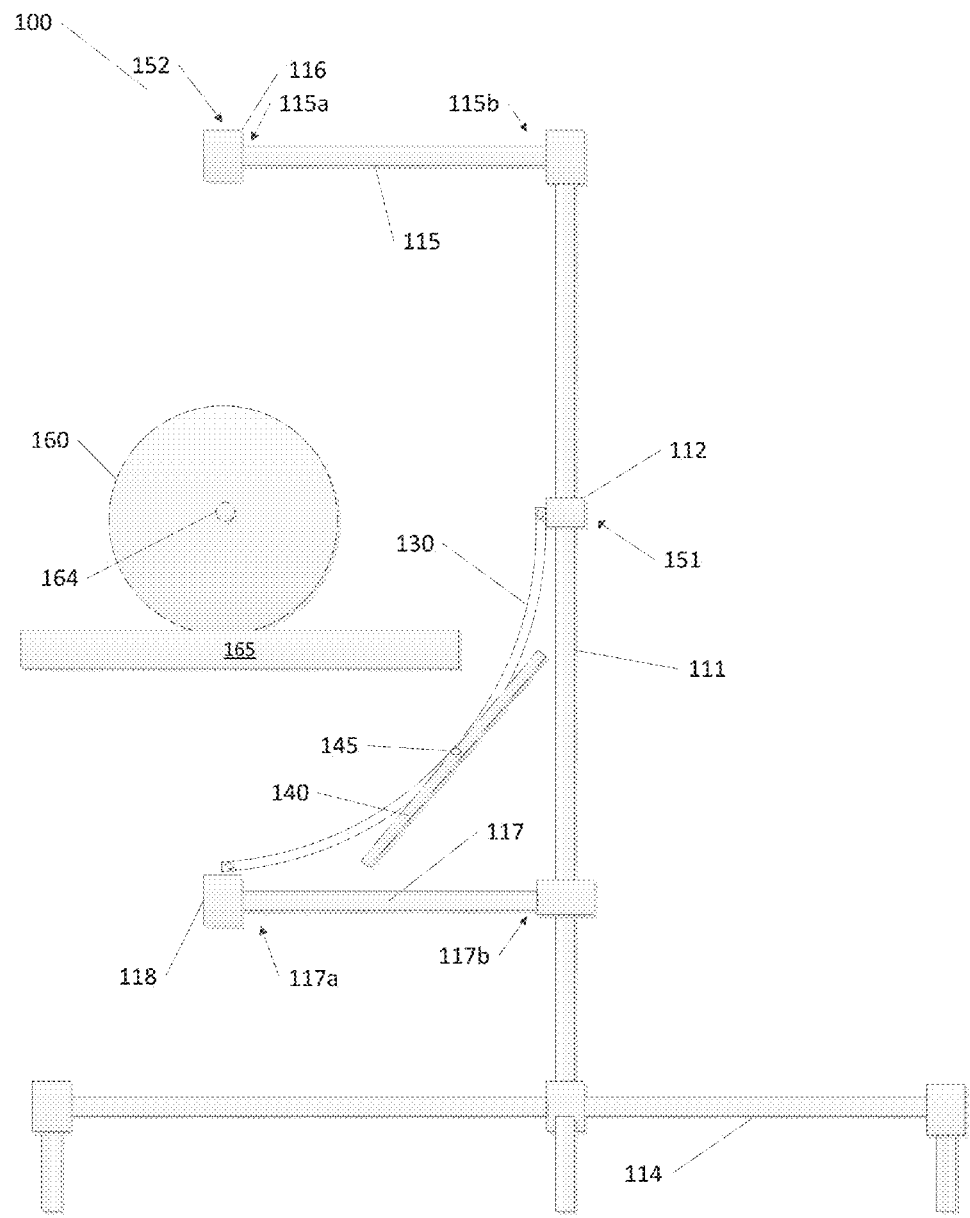
Figure 1C:
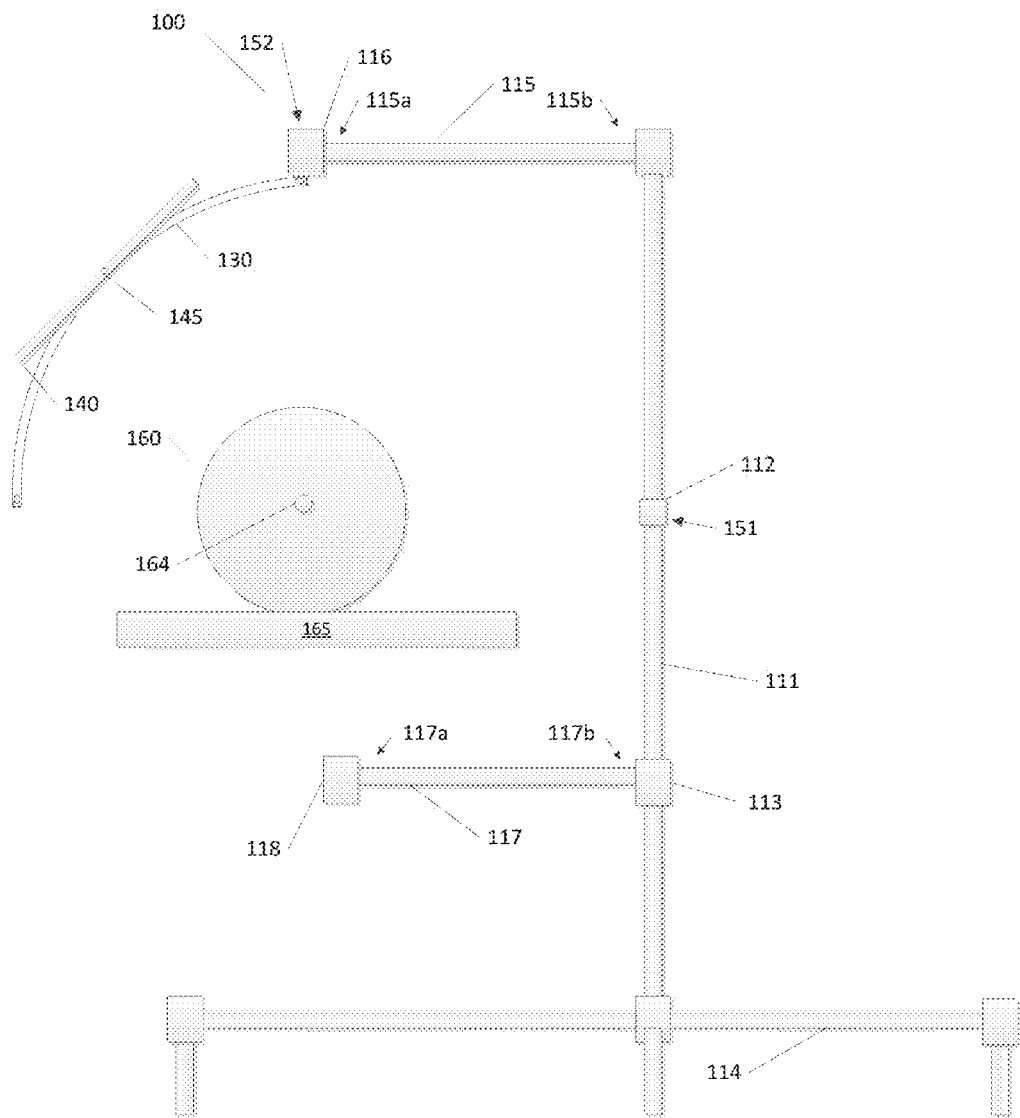
Figure 1D:
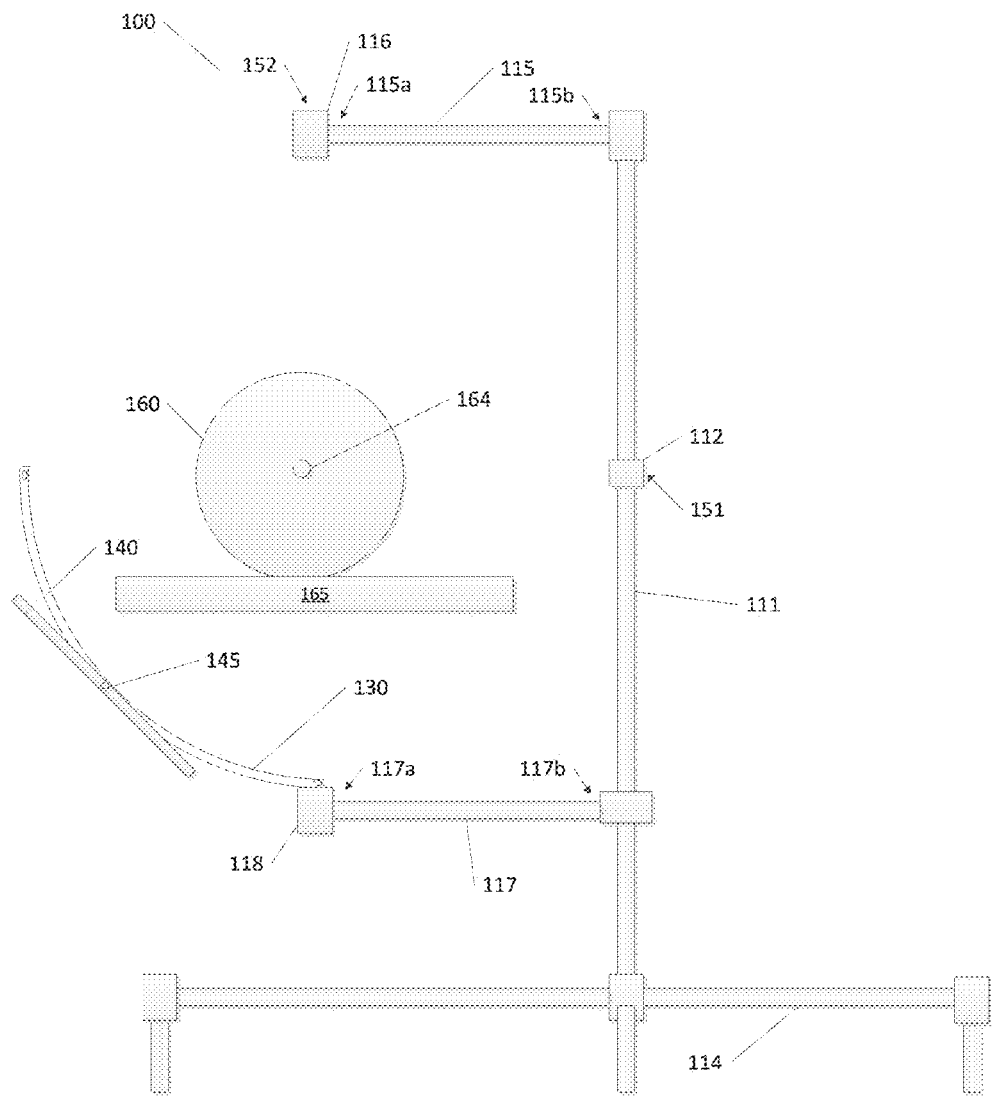
Figure 1E:
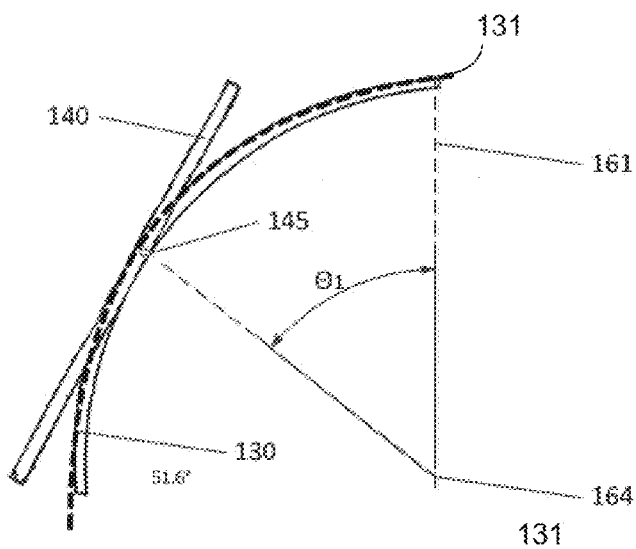
FIGS. 1E to 1G illustrate a schematic side view of a frame segment and a clearance member coupled to the frame segment at three different positions.
Figure 1F:
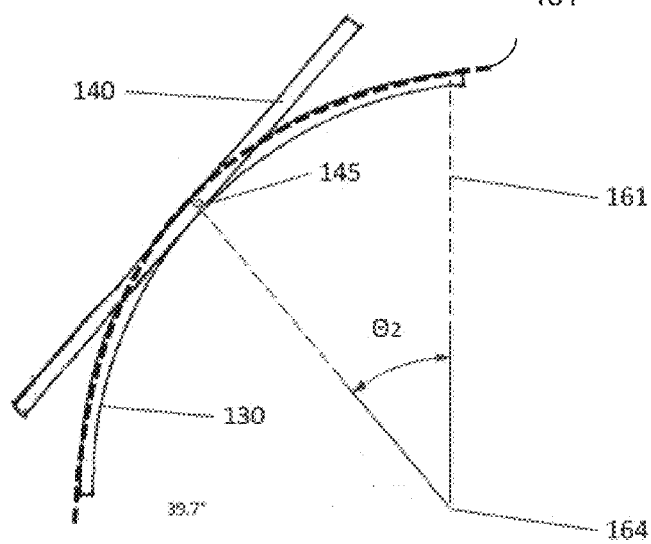
Figure 1G:
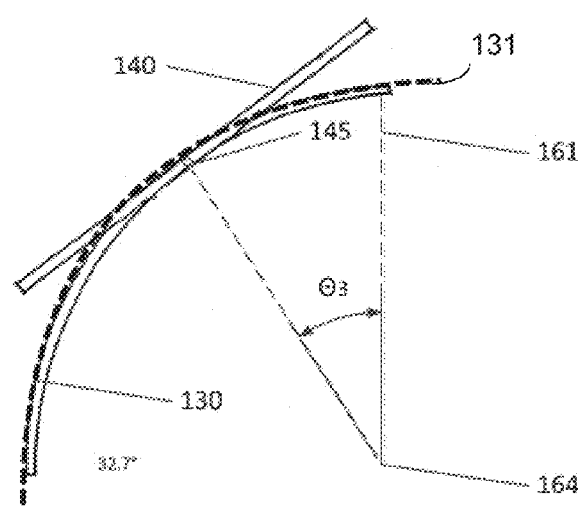

As described above, the represented component is intended to orbit at least partially around patient 160. To account for the position of the component along the orbital path, clearance member 140 can be selectively adjusted along the clearance member mount and secured at a selected position that would correspond to a position along the orbital path. The points on the clearance member mount, at which clearance member 140 can be secured, are disposed along a line or curve that corresponds to a portion of the orbital path. For example, FIGS. 1E to 1G depict clearance member 140 in three different positions along a curve 131 that extends along the length of frame segment 130, wherein clearance member 140 projects out of the page. Clearance member 140 can be incrementally adjusted or continuously adjusted. For example, in some embodiments, clearance member 140 comprises an attachment feature 145—such as a ball detent pin—that are configured to selectively couple clearance member 140 to frame segment 130 at two or more sites along frame segment 130. In various embodiments, clearance member 140 can comprise a plurality of attachment features 145—such as two ball detent pins—that protrude from clearance member 140 near to but spaced apart from each other. The two pins can be inserted into two appropriately-spaced bores 146 (as illustrated in the embodiment shown in FIGS. 2A and 2B) amongst a plurality of two appropriately-spaced bores 146 on frame segment 130. Inversely, clearance member 140 can comprise two appropriately-spaced bores as attachment features 145 and frame segment 130 can comprise a plurality of two protruding ball detent pins that can extend into the two appropriately-spaced bores. In other embodiments, clearance member 140 can be slidably adjusted along the length of frame segment 130. For example, frame segment 130 can be operable as a track, and attachment feature 145 can comprise a track mount and a set screw so that clearance member 140 can slide along frame segment 130 and be securely set. While only two examples are described, any variety of suitable mechanisms and arrangements can be used to selectively couple clearance member 140 to frame segment 130.

A location where clearance member 140 is couplable to frame segment 130 can be defined as an angle that corresponds to the angular position of the medical device component, e.g., the gantry angle (0° being the top of the orbital path and coincident with attachment feature 116). To facilitate measurement of this angle, in various embodiments, frame segment 130 can operate as a protractor. The angle measured is the angle Θ formed by the line (or radius) between attachment feature 145 (or a comparable location in embodiments where attachment feature 145 does not correspond to the portion of mimicked medical device component from where gantry angle would be measured) and isocenter 164 and substantially vertical axis 161 that passes through isocenter 164 as illustrated in FIGS. 1E to 1G via $Θ_1$, $Θ_2$, and $Θ_3$. The measured angle Θ corresponds to the component angle (such as a gantry angle) along the orbital path.

Also described above, during use of the medical device, object 160/165 can be rotatable about isocenter 164 and therefore askew to the medial device's orbital axis. To account for the angle of object 160/165 without having to actually move object 160/165, frame segment 130 can be rotated relative to vertical axis 161. For example, as shown in FIG. 3A, the couch angle is approximately 30° relative to the orbital axis of the gantry, and the gantry angle is 90°. In comparison, as shown in FIG. 3B, to account for this couch angle, the frame segment 130 is rotated a corresponding 30° about vertical axis 161 relative to horizontal support 115. As such, the angle of frame segment 130 relative to horizontal support 115 should generally correspond to the couch angle. In addition, to account for the gantry position, clearance member 140 is positioned at 90° on frame segment 130.

To facilitate this object angle adjustment, in various embodiments, frame segment 130 is rotatably coupled to a horizontally oriented portion of device 100, like horizontal support 115. Frame segment 130 can extend downward or upward from horizontal support 115 and is rotatably coupled to horizontal support 115 via an attachment feature 116. Furthermore, the end 115a of horizontal support 115 to (or near) which frame segment 130 is coupled is opposite the end 115b to (or near) which horizontal support 115 is coupled to upright support 111. During use, frame segment 130 can be selectively rotated about vertical axis 161 (which extends through attachment feature 116) and can be at least semi-securely set at a chosen angle. For example, attachment feature 116 can comprise a click-stop mechanism that permits frame segment 130 to rotate in one or both directions and click to incremental stops of 0.1°, 0.5°, 1°, 2°, 3°, 5°, or more. Alternatively, frame segment 130 can be continuously rotated about a flanged pin. For example, attachment feature 116 can comprise a flanged pin that extends downwardly from horizontal support 115 and into and/or through a hole defined by frame segment 130 with frame segment 130 being supported by the flange and rotatable about the pin. On the end opposite the flange, the pin is threaded to receive an oppositely threaded nut that can be used to securely set frame segment 130 at a chosen angle. In another embodiment, with reference to FIGS. 2C(i) and 2C(ii), device 100 can further comprise a plate 170 that is disposed adjacent to (such as between) horizontal support 115 and frame segment 130 and coupled (e.g., secured) to horizontal support 115. In addition, frame segment 130 can comprise an arm 132 laterally extending from frame segment 130 near plate 170 such that arm 132 is rotatable about vertical axis 161. Arm 132 can be configured to couple to plate 170 to selectively and securely engage with plate 170, e.g., by engagement with a one of a plurality of detents or holes 172, defined by plate 170. In the embodiment shown, a pin 174, such as a detent pin, can extend into hole 172 and into hole 134 defined by arm 132 to set the position of frame segment 130. While only three examples are described, any suitable mechanism or arrangement can be used to rotatably couple frame segment 130 to horizontal support 115 and to set frame segment 130 at a selected angle relative to horizontal support 115.

In order to measure the angle of rotation, device 100 can further comprise another protractor operable to measure the angle of the frame segment 130 relative to the horizontal support. For example, again with reference to FIGS. 2C(i) and 2C(ii), such a protractor can be plate 170 that is disposed adjacent to (such as between) horizontal support 115 and frame segment 130 and coupled (e.g., secured) to horizontal support 115. While not shown, markings can be disposed on plate 170 that correspond to the couch angle. FIG. 2C(i) illustrates frame segment 130 at the 0° position corresponding to a 0° couch angle, and FIG. 2C(ii) illustrates frame segment 130 at about the 15° position corresponding to about at 15° couch angle. Alternatively, such a protractor can be integral to the click-stop mechanism. To allow for rotation, frame segment 130 can be detachable from the upright support 111.

Frame segment 130 is configured to define curve 131 so that clearance member can be positionable along a portion of the orbital path. In various embodiments, frame segment 130 is an arced frame segment such that defines an arc on an inner surface, an outer surface, or a lateral surface. Arced frame segment 130 can define an arc of about 10° to about 360°. In various embodiments, frame segment 130 defines approximately a 45°, 90°, 180°, 270°, or 360° arc. While illustrated herein as an arced or annular shape, frame segment 130 can comprise any shape that defines a curve that corresponds to an orbital path. The orbital path could be any variety of lines, angles, or shapes, and frame segment 130 can be configured to correspond thereto. The angle of frame segment 130 relative to horizontal support 115 corresponds to the object angle, e.g., the couch angle. The present clearance member mounts can have any variety of shapes other than a frame-like structure, such as frame segment 130. The clearance member mount (which may comprise multiple components coupled together) need only provide a surface to which a clearance member (e.g., clearance member 140) is couplable at plurality of points so that the clearance member is positionable along a curved path that has a radius that is equal to or less than the clearance radius of the represented component, such as the treatment head of a linac or other medical device component.

Frame segment 130 and/or clearance member 140 can be appropriately dimensioned for the medical device component for which a clearance test is desired. In various embodiments, the points at which clearance member 140 is couplable to frame segment 130 define curve 131 so that clearance member 140 is positionable at a plurality of points along a curved path that has a radius that is equal to or less than the clearance radius of the represented component, such as the treatment head of a linac or other medical device component. In such embodiments, curve 131 can define a radius that is greater than, equal to, or less than the clearance radius of the represented component, as the radius of curve 131 ultimately depends on the dimension and configuration of clearance member 140. In various embodiments, the radius can be defined as the distance between clearance member 140 (at attachment feature 145) and isocenter 164 and can be approximately 20 centimeters ("cm"), 21 cm, 22 cm, 23 cm, 24 cm, 25 cm, 26 cm, 27 cm, 28 cm, 29 cm, 30 cm, 31 cm, 33 cm, 34 cm, 35 cm, 36 cm, 37 cm, 38 cm, 39 cm, 40 cm, 41 cm, 42 cm, 43 cm, 44 cm, 45 cm, 46 cm, 47 cm, 48 cm, 49 cm, 50 cm, 51 cm, 52 cm, 53 cm, 54 cm, 55 cm, 56 cm, 57 cm, 58 cm, 59 cm, 60 cm, or any amount between these possible distances. For example, the clearance radius for most Varian Medical C-arm linacs is about 42 to about 44 cm. The stated values are to serve as examples and should not to be construed as limiting.

Clearance member 140 is oriented relative to frame segment 130 so that a plane in which frame segment 130 is positioned is perpendicular to a plane in which clearance member 140 is positioned. In addition, in some embodiments, a surface of clearance member 140 can be generally tangent to an arced inner or an arced outer surface of frame segment 130. In various embodiments, clearance member 140 can be coupled to the inner surface or outer surface of frame segment 130. However, in other embodiments, clearance member 140 can be coupled to a lateral surface of frame segment 130, as shown in the embodiment illustrated in FIGS. 2A and 2B. For example, with reference to FIGS. 1E and 1G, clearance member 140 can be a half disc or semi-circular arced structure coupled to the lateral surface of frame segment 130 and extending outwardly therefrom (i.e., projecting out of the page).

The shape of clearance member 140 depends to some extent on the medical device component for which it is serving as a spatial substitute. With reference to FIGS. 2A and 2B, an isocenter-facing portion 142 and/or edge 144 of clearance member 140 can generally define a profile that generally or substantially mimics a portion of the medical device component's profile. In various embodiments, a portion of clearance member 140 can define a shape that has a similar outer edge(s) 144 and/or a protruding surface(s) of at least a portion of the represented component that is likely to collide with object 160/165. In some embodiments, clearance member 140 can be an arced member. In addition, isocenter-facing portion 142 of clearance member 140 can define a planar surface, such as, by comprising a disc, half disc, quarter disc, or any other fraction of a disc. Clearance member 140 can comprise a lattice material or film material that is supported by a frame. In various embodiments, the lattice or film can define an isocenter-facing portion 142 that substantially mimics a portion of the medical device component's profile. Furthermore, clearance member 140 can be configured to be rotatably coupled to frame segment 130 so that clearance member 140 can rotate through a plane to check other sections where the represented component has the potential to collide. For example, an embodiment of clearance member 140 that comprises a quarter disc or quarter arc can occupy a first Cartesian quadrant but then be rotated to occupy a second Cartesian quadrant. Similarly, clearance member 140 can be a bar that is configured to sweep through a plane.

Similarly, the dimensions of clearance member 140 depend to some extent on the medical device component for which it is serving as a spatial substitute. In various embodiments, clearance member 140 can have a width or define an arc that has a radius of about 5 cm up to about 50 cm. For example, the treatment head for most Varian Medical C-arm linacs defines an outer edge arc that has a radius of about 40 cm and thus clearance member 140 would also have a radius of about 40 cm. The stated range serves an example and should not to be construed as limiting. In various embodiments, the represented medical device component can comprise any component that operates on a c-arm. For example, the medical device component can be the treatment head/collimator of a linac. Examples of c-arm linacs include Varian Electra and Siemens. Frame segment 130 and/or clearance member 140 can be configured to have the appropriate dimensions of the medical device component for which a clearance test is desired.

For more extreme object angles, e.g., angles at or near 90° or 270° (as shown in FIGS. 3C and 3D, respectively), frame segment 130 rotation can be impeded by the object 160/165, such as the patient 160 or the couch 165 upon which the patient 160 can be lying. In order to achieve the desired rotation, in various embodiments, frame segment 130 can be selectively shifted along the orbital path or shortened in length. For example, in some embodiments, frame segment 130 can comprise at least two interconnected members that can be selectively coupled and decoupled to shorten and extend frame segment 130 as needed. In the same or different embodiments, frame segment 130 can be configured to be selectively coupled to horizontal support 115 at two or more sites along frame segment 130 to facilitate shifting frame segment 130's position and be rotatable at each selected position. For example, attachment feature 116 can comprise a pin with at least two ball detents that can be inserted into and retracted from one of a plurality of bores or openings in frame segment 130. Frame segment 130 can be configured to rotate about the pin. In other embodiments, attachment feature 116 is coupled to the horizontal support and comprises a guide or track through which frame segment 130 is slidable to facilitate shifting frame segment 130's position. The guide or track can be configured to be rotatable along with frame segment 130. Again, while only a few examples are described, any variety of suitable mechanisms and arrangements can be used to selectively couple frame segment 130 to horizontal support 115 while being rotatable at each selected position.

Alternatively, to test for clearance when object angles are at approximately 90° or 270°, frame segment 130 can be rotatably coupled to the upright support 111 and detachable from the horizontal support 115, and clearance member 140 can be positioned on frame segment 130 at the top of frame segment 130 (the 0° position). In this manner, frame segment 130 can be selectively rotatable about a substantially horizontal axis 162 that extends through attachment feature 112 at upright support 111 and may also be configured to be securely set in a given position. To measure the angle of rotation of frame segment 130 relative to upright support 111, device 100 can comprise a third protractor. Such a protractor can be configured in the same manner as that described for the protractor to measure the angle of frame segment 130 relative to horizontal support 115. In some embodiments, the measured angle in this configuration corresponds to the angle of the represented component, e.g., the gantry angle.

To facilitate alignment of frame segment 130 in advance of clearance testing, device 100 can further comprise at least two alignment targets, e.g., 2, 3, 4, or more. (The approximate locations of alignment target 151/152 are indicated on FIGS. 1A to 1D and FIGS. 2A to 2B but are not visible in the view shown.) In various embodiments, at least two set-up lasers can be arranged in the room where clearance testing is conducted. The approximate intersection of the two lasers represents the location of isocenter 164. A first laser can be positioned to be perpendicular to the orbital axis. A second laser can be positioned to align with the axis of rotation of couch 165. In some embodiments, a third laser can be positioned opposite the first laser. During use, an alignment target should intersect with one of the set-up lasers. In various embodiments, a first alignment target 151 is located on upright support 111. Alignment target 151 can be located approximately the same distance above the floor as that of isocenter 164, or upright support 111 can be vertically adjustable, such as with telescoping members, to enable alignment. In various embodiments, the distance between the floor and isocenter 164 is approximately 100 cm, 110 cm, 120 cm, 125 cm, 130 cm, 135 cm, 140 cm, 145 cm, 150 cm, 160 cm, or 170 cm, or any amount between these distances. In various embodiments, such distance is from approximately 125 cm to approximately 135 cm. The stated values are to serve as examples and should not to be construed as limiting. A second alignment target 152 can be located on frame segment 130 or horizontal support 115 and aligned with vertical axis of rotation 161 of frame segment 130. The above-described lasers (in addition to other lasers that are traditionally used for patient alignment) can be used to facilitate patient alignment before device 100 is positioned. To further enhance the accuracy of alignment, one or more of the set-up lasers can project a two-dimensional shape, e.g., a cross-hair shape, and one or more of the alignment targets can comprise a corresponding two-dimensional marking configured to align with the projected two-dimensional shape of the set-up laser. In other embodiments, alignment target 151/152 can be a radiation detector that is configured to indicate an intersection with the laser. As an example, first alignment target 151 may be positioned so as to align with a sagittal laser and second alignment target 152 may be positioned to align with a coronal laser during use of device 100.

In various embodiments, device 100 can be supported by the floor. For example, as shown in FIGS. 1A-1D and FIGS. 2A-2B, device 100 can comprise a base 114 that supports upright support 111. In various embodiments, with reference to FIGS. 2A and 2B, one or more adjustable leveling feet 180 can be couplable to base 114 to define the surfaces that contact the floor or other underlying supporting surface. In various embodiments, each leveling foot 180 can be adjusted by rotating foot 180 to extend or to retract foot 180 relative to base 114. Alternatively, to facilitate easier access to adjust leveling feet 180, an adjustment member, such as a knob 185, can be disposed adjacent an upper surface or a lateral surface of base 114, can be couplable to a respective leveling foot 180, and can be configured to be rotated or displaced to thereby cause foot 180 to extend or to retract foot 180 relative to base 114. In various embodiments, one or more leveling feet 180 can comprise a slip resistant material defining the surface that contacts the floor or other underlying supporting surface. Also, in various embodiments, base 114 can comprise a plurality of legs that extend radially relative to upright support 111. The length of legs 182 of base 114 can be adjusted to accommodate different spaces or to improve stability of device 100.

In other embodiments, device 100 can be attached to couch 165. For example, as shown in FIG. 4, upright support 111 can be coupled to a clamp 170 (e.g., a c-clamp) and, more specifically, slidably coupled to clamp. Clamp 170 can be coupled to (e.g., fixed to) couch 165 upon which patient 160 is positioned. In various embodiments, upright support 111 can be vertically adjusted with respect to couch 165. For example, clamp 170 can define an opening through which the upright support 111 can slidably extend and have a securement mechanism to set the vertical position of clamp 170 relative to upright support 111. In addition, clamp 170 can comprise a threaded bore in communication with an opening and a set screw threadable through the bore to fix the vertical position of clamp 170 relative to upright support 111. Alternatively, couch 165 can comprise a track extending along at least a portion of the length of couch 165, and upright support 111 can be coupled thereto via a track mount and a set screw so that upright support 111 can slide along couch 165 and be securely set. While only two examples are described, any variety of suitable mechanisms can be used to secure the upright support 111 to couch 165, to facilitate vertical adjustment of upright support 111, and/or to facilitate longitudinal movement of device 100.

To facilitate testing for clearance on the underside of object 160/165, clearance check device 100 can further comprise second horizontal support 117, as shown in FIG. 1A to 1D. Second horizontal support 117 can comprise a first end 117a and a second end 117b and be coupled to and extend from upright support 111, such as via attachment feature 118. First horizontal support 115 and second horizontal support 117 are aligned but spaced apart an amount slightly greater than the diameter of the orbital path so that frame segment 130, when coupled to one or both horizontal supports 115 and 117, is properly positioned for clearance testing. Frame segment 130 can be configured to slidably and/or rotatably coupled to second horizontal support 117 near first end 117a. When coupled in this manner, frame segment 130 extends upward from second horizontal support 117. Frame segment 130 can be configured to be selectively rotatable about substantially vertical axis 161 (which passes through attachment feature 118) and may also be configured to be securely set at a chosen angle. In a different or the same embodiment, frame segment 130 can be slidably coupled to second horizontal support 117 so that it can slidably adjust to correspond to a different section of the orbital path. The attachment mechanisms that can be used to couple frame segment 130 to horizontal support 117 (such as via attachment feature 118) can be the same or different as those described above for coupling frame segment 130 to horizontal support 115.

Other embodiments can be used as a clearance check device when the couch 165 angle is at or near 0°. In such scenarios, clearance member 140 as described above is not used. Instead, frame segment 130 itself can be utilized as the spatial reference. For example, FIG. 5 depicts an embodiment of a clearance check device 400 comprising upright support 111 and frame segment 130 coupled to upright support 111 and extending laterally therefrom. When properly aligned next to an object 160/165, frame segment 130 can be used to indicate potential collisions between the medical device component and object 160/165, the medical device component being intended to orbit about object 160/165. As such, frame segment 130 can be dimensioned so that its inner surface defines an arc comprising a radius that is substantially equal to or less than the orbital radius of the centermost portion of a represented component moveable along the orbital path. As such, during use, contact between frame segment 130 and an object 160/165 indicates a potential collision between object 160/165 and the represented component. For example, the represented medical device component can be a treatment head of a linac, the object 160/165 can be patient 160 lying on couch 165, and during use, contact between the frame segment 130 and the patient 160 indicates a potential collision between the patient 160 and the represented medical device component.

As with frame segment 130 of device 100, in various embodiments, frame segment 130 of device 400 can define an arc. Arced frame segment 130 can define any angle from about 10° to about 360°. In various embodiments, frame segment 130 defines approximately a 45°, 90°, 180°, 270°, or 360° arc. Arced frame segment 130 comprises a radius that is equal to or less than a clearance radius of the orbiting medical device component. While described in terms of an arc, it is also contemplated that an orbital path could be any variety of lines, angles, or shapes, and frame segment 130 can be configured to correspond thereto. In various embodiments, as shown in FIG. 6, arced frame segment 130 is an annular frame.

To facilitate frame segment 130 shifting to a different section of the orbital path, frame segment 130 of device 400 can be configured in the same manner previously described for device 100. For example, in various embodiments, clearance check device 400 can further comprise horizontal support 115 having a first end 115a and a second end 115b and being coupled to and extending from upright support 111 near second end 115b. Frame segment 130 of device 400 can be slidably and/or rotatably coupled to horizontal support 115 at or near second end 115b and extending downward. Frame segment 130 can be selectively rotatable about a substantially vertical axis 161 that passes through the attachment feature 116 at horizontal support 115 and configured to securely set. To allow for rotation, frame segment 130 can be detachable from the upright support 111. In a different or the same embodiment, frame segment 130 can be slidably coupled to horizontal support 115 so that it can slidably adjust to correspond to a different section of the orbital path.

Similarly, like frame segment 130 of device 100, in various embodiments, frame segment 130 of device 400 can be slidably and/or rotatably coupled to the upright support 111 and detachable from horizontal support 115. Frame segment 130 can be selectively rotatable about a substantially horizontal axis 162 that passes through an attachment feature 112 at upright support 111 and configured to securely set. In a different or the same embodiment, frame segment 130 can be slidably coupled to upright support 111 so that it can slidably adjust to correspond to a different section of the orbital path.

Like device 100, in various embodiments, clearance check device 400 can further comprise a second horizontal support 117 having a first end and a second end and being coupled to and extending from upright support 111 at the first end. First horizontal support 115 and second horizontal support 117 are spaced apart an amount slightly greater than the diameter of the orbital path so that the inner surface of frame segment 130, when coupled to one or both horizontal supports 115, 117, corresponds to a portion of the orbital path for purposes of clearance testing. Frame segment 130 of device 400 can be slidably and/or rotatably coupled to second horizontal support 117 near the second end. When coupled, frame segment 130 extends upward from second horizontal support 117. Frame segment 130 can be selectively rotatable about vertical axis 161 that passes through the attachment feature 118 at second horizontal support 117 and configured to securely set. In a different or the same embodiment, frame segment 130 can be slidably coupled to second horizontal support 117 so that it can slidably adjust to correspond to a different section of the orbital path.

In various embodiments, in certain situations, the position of frame segment 130 of device 400 may be adjusted to account for the position of the represented component along the orbital path. For example, if the arc (represented by an arced version of frame segment 130) when coupled to horizontal support 115 and to upright support 111 was located in Quadrant I but the represented component was to be positioned in Quadrant II, then to test for clearance in Quadrant II, the position of frame segment 130 should be shifted to Quadrant II. In order to facilitate such a shift, frame segment 130 can be slidably or rotatably adjusted with respect to horizontal support 115 and upright support 111. In addition, frame segment 130 can be incrementally or continuously adjusted. The previously described mechanisms for coupling frame segment 130 to upright support 111 and/or horizontal support(s) 115 and 117 can be similarly implemented.

As in device 100, to facilitate alignment of frame segment 130, device 400 further comprises at least two alignment targets 151, 152 (The approximate locations of alignment target are indicated on FIGS. 5 and 6 but are not visible in the view shown.) In addition, at least two set-up lasers should be arranged in the room where clearance testing is conducted. One of the lasers should be perpendicular to the orbital axis, and the other laser should intersect the orbital axis at about 90°. The intersection of the lasers represents the location of isocenter 164. During use, an alignment target 151/152 should indicate an intersection with a set-up laser. For example, alignment target 151/152 can be a cross-hair marking such that intersection is visibly determined. In other embodiments, alignment target 151/152 can be a radiation detector that is configured to indicate an intersection with the laser. In various embodiments, a first alignment target 151 is located on upright support 111. Alignment target 151 can be located approximately the same distance above the floor as that of isocenter 164. Alternatively, upright support 111 can be vertically adjustable, such as with telescoping members, to enable alignment. In a further embodiment, a second alignment target 152 is located on frame segment 130 or horizontal support 115. The above-described lasers (in addition to other lasers that are traditionally used for patient alignment) can be used to facilitate patent alignment before device 400 is positioned.

With reference to FIG. 6, as with device 100, clearance check device 400 can, in some embodiments, also comprise second upright support 119, where frame segment 130 spans a space between and is securely coupled to first and second upright supports 111 and 119, respectively. Frame segment 130 can be an arced or annular frame. Again, arced frame segment 130 or annular frame segment 130 comprises a radius that is substantially equal to or less than a clearance radius of the represented medical device component. In some embodiments, a third alignment target (not shown) can be located on second upright support 119, also the same distance above the floor as that of isocenter 164. A third laser to intersect the third alignment target can be positioned opposite the laser that intersects with target 151.

In various embodiments, like device 100, device 400 can be supported by the floor. For example, as shown in FIG. 5, device 400 can comprise a base 114 that supports upright support 111. In other embodiments, device 400 can be attached to couch 165. For example, couch 165 can comprise a track extending along at least a portion of the length and upright support 111 can be coupled thereto via a track mount and a set screw so that clearance member 140 can slide along frame segment 130 and be securely set. Also, a clamp as previously described above can also be used. While only two examples are described, any variety of suitable mechanisms can be used to secure upright support 111 to couch 165, to facilitate vertical adjustment of upright support 111, and/or to facilitate longitudinal movement of device 400.

In various embodiments, the clearance check device of the present disclosure can be configured to interchange frame segment 130 and/or clearance member 140 to account for the varying clearance radii (due to varying orbital paths) and/or varying shape or dimension of the represented component. For example, frame segment 130 and/or clearance member 140 can be interchanged with one of a different dimension, and the location of attachment of the segment and/or member to upright support 111 and/or horizontal support(s) 115 and 117 can be adjusted to the dimension of the selected segment or member, as needed. Accordingly, another aspect of the present disclosure can comprise a clearance check kit having a clearance check device in accordance with the present disclosure and multiple frame segments and/or clearance members. For example, a kit can comprise a first frame segment 130 and/or clearance member 140 dimensioned to test for clearance of a first component having a first orbital path and a second frame segment 130 member and/or clearance member 140 dimensioned to test for clearance of a second component having a second orbital path.

Another aspect of the present disclosure comprises a method of using a clearance check device. For example, one such method can comprise positioning a patient on a patient-support structure (such as a couch); positioning a clearance check device comprising a frame segment positioned relative to the patient so that the frame segment substantially aligns with a transverse plane that passes through a treatment target in or on the patient; and testing for contact between the clearance check device and the patient or the patient-support structure.

In various embodiments, positioning the patient on the patient-support structure can comprise aligning the patient with at least two lasers (e.g., in-room lasers) that emit beams that are substantially perpendicular. For example, a patient's skin can be marked with alignment targets so that, when properly positioned, the treatment target and isocenter 164 substantially coincide.

Similarly, positioning the clearance check device can comprise aligning the clearance check device with the at least two lasers (e.g., in-room lasers) and can involve vertically adjusting the frame segment. In the same or different embodiments, positioning the clearance check device can comprise aligning the base, such as the feet of the base, of the clearance check device with alignment reference marks on the floor.

To expedite the clearance check procedure, testing for contact can involve first identifying the range of possible positions or coordinates where the represented component will be located. For example, for non-coplanar, static gantry treatment types, a preselected template (such as a known set of beam positions that translate to a known set of gantry angles and couch angles) can be tested with the clearance check device. A specific template can correspond to a specific region or anatomy of the body. Thus, once a treatment target is identified, a known template for that particular region can be selected and tested. Once the possible positions are determined, the clearance check device can be adjusted to check for clearance for each of the possible positions, or for the extreme positions where a collision is more likely. If the clearance check fails, the clearance check device can be used to determine alternative positions that are collision-free.

In the context of a procedure using a linac, one or more coordinates (such as a gantry angle and/or a couch angle) can be preselected for a treatment procedure. For each of the identified coordinates, testing for contact using some embodiments of the present clearance check devices can comprise positioning clearance member 140 along frame segment 130 to a position defined by an angle. This angle represents the gantry angle. Similarly, frame segment 130 can be rotated about vertical axis 161 that passes through the treatment target, toward a preselected angle. This angle represents the couch angle. Clearance is confirmed if no contact is made between clearance member 140 and patient 160 at the tested coordinates. If contact between patient 160 and clearance member 140 is made, device 100 can be used to determine alternative, collision-free coordinates that are comparable or close to the failed coordinates. Stated differently, the identified couch angle or the identified gantry angle of the preselected treatment procedure can be modified based upon the angle of rotation of frame segment 130 or the position of clearance member 140 just prior to contact being made. For example, the alternative coordinates can be obtained by adjusting the couch angle and/or the gantry angle by an amount from about 0.5° to about 10° from the angles at which contact was detected. This clearance method can be used when the identified couch angle is an angle from about 0° to about 90° and/or about 270° to about 360° (0°).

In some embodiments, testing for contact at an identified couch angle (e.g., couch 165 angle) of about 90° or about 270° can involve a slightly different method. For these extreme couch angles, clearance member 140 can be released from horizontal support 115 and securely positioned at the 0° degree position on frame segment 130. Frame segment 130 can then be rotated about horizontal axis 162 that passes through the treatment target to an angle that substantially corresponds to the preselected gantry angle or to the point at which contact is made. Again, clearance is confirmed if no contact is made between clearance member 140 and patient 160 at the tested coordinates. If contact between patient 160 or couch 165 and clearance member 140 is made, an alternative gantry angle can be determined based upon frame segment 130's angle of rotation just prior to contact with patient 160 or couch 165. For example, the alternative angle can be obtained by adjusting the gantry angle an amount from about 0.5° to about 10° from the angle at which contact was detected.

In some embodiments, treatment may comprise translating patient 160 and couch 165 along a horizontal axis of couch 165 (longitudinally) or a transverse axis of couch 165 (laterally). For such treatments, a clearance check can be performed by similarly translating patient 160 and couch 165 alongside a stationary clearance check device 100, once clearance member 140 and/or frame segment 130 are set to the preselected coordinates. Alternatively, frame segment 130 and/or clearance member 140 can be translated longitudinally or laterally to account for this type of movement, once clearance member 140 and/or frame segment 130 are set to the preselected coordinates.

In such cases, a potential collision is indicated when contact between frame segment 130 and object 160/165 will or does occur. In some embodiments, detecting contact can comprise visually inspecting for contact between the clearance check device and patient 160 or couch 165. In the same or different embodiments, detecting contact can occur by way of a sensor configured to detect contact and may further include a computer to record the coordinates at which contact was made. In some embodiments, detection of contact can cause a visual or audible alarm to be triggered.

EXAMPLES

Annular Frame Clearance Check Device—Construction and Testing: A clearance check device in accordance with the embodiment shown in FIG. 6 and described herein was constructed. An annular frame or hoop was fashioned with an inner radius substantially equal to the distance between the isocenter and the nearest portion of the head of a Linac. This ring was mounted to a stand having an upright support that was configured for variable vertical positioning.

To use the device, the annular frame is placed around the patient and is aligned with the patient alignment lasers. The patient is moved back and forth longitudinally within the ring. During this movement, if the annular frame touches any portion of the patient, couch, or patient positioning aids, a collision between these and the Linac head will likely occur. Ten test runs were conducted. Nine of out of then ten runs predicted collisions with the Linac head and gave an additional millimeter of clearance.

Clearance Check Device with Frame Segment with Clearance Member—Testing: A clearance check device in accordance with the embodiment shown in FIGS. 2A to 2B and described herein was constructed. A L-shaped frame segment defining a 90° arc along its length was created. A mock half-Linac head was also created. The mock Linac head was configured to couple to the frame segment at one end. The frame segment and mock half-Linac head were configured so that the head frame would be couplable to the frame segment at a plurality of points along the length of the frame segment. The position of the mock half-Linac head when coupled to the frame segment was spaced apart from the isocenter a distance that was substantially equal to the clearance radius of the Linac head. This frame segment was mounted to a stand having an upright support and a horizontal support. The frame segment extended downward from the horizontal support and was rotatably coupled thereto. The angle of the frame segment relative to the horizontal support mimicked the couch angle.

To use the device, the patient is aligned with the alignment lasers. Next, the device is positioned next to the patient and the frame segment is aligned with the patient alignment lasers. The frame segment can be rotated to mimic the couch angle. The mock half-Linac head can be coupled to the frame segment at a position along the segment to mimic the desired gantry angle. The frame segment is then rotated until the mock half-Linac head frame touches any portion of the patient, couch, or patient positioning aids. The mimicked couch angle and gantry angle can be recorded.

In testing, a volunteer was placed on the couch using the same patient setup devices typically used for lung stereotactic body radiosurgery (SBRT), which includes a bean bag, an abdominal compression device, pillows for elevating the knees, a head holder, and a t-shaped device placed superior to the head for the patient to hold. A number of isocenters were marked in places likely at the extremes of the volunteer's lungs. The volunteer was aligned with the alignment lasers at the first isocenter to be tested. The clearance check device was aligned to this same isocenter and a typical beam geometry for lung SBRT was tested for collisions by rotating the frame segment, with a mock half-Linac head coupled thereto, to mimic the couch angle. The frame segment was moved until the mock half-Linac head collided with the volunteer, a positioning aid, or with the couch. The angle of collision was recorded. This was repeated for each marked isocenter. Usage of this device prevented all collisions, for all isocenters and beam geometries tested.

The above specification and examples provide a complete description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the illustrative embodiments of the present clearance check devices, systems, and methods are not intended to be limiting. Rather, the present devices, systems, and methods include all modifications and alternatives falling within the scope of the claims, and embodiments other than those shown may include some or all of the features of the depicted embodiments. For example, components may be combined as a unitary structure and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not to be interpreted as including means-plus- or step-plus-function limitations, unless such a limitation is explicitly recited in a given claim using the phrase(s) "means for" or "step for," respectively.

The invention claimed is:

1. A clearance check device comprising:
   an upright support;
   a frame segment couplable to the upright support, the frame segment having a surface defining an arc that has a radius that, when the frame segment is coupled to the upright support, is substantially equal to or less than an orbital radius of a centermost portion of a medical device component moveable along an orbital path during radiation delivery.

2. The clearance check device of claim 1, further comprising at least two alignment targets couplable to different portions of the clearance check device.

3. The clearance check device of claim 1, further comprising a horizontal support configured to extend from the upright support, the frame segment being couplable to the horizontal support.

4. The clearance check device of claim 3, where the frame segment is rotatably couplable to the upright support, and releasably couplable to the horizontal support, such that the frame segment can be rotated about a horizontal axis that passes through the upright support.

5. The clearance check device of claim 4, further comprising a second horizontal support couplable to or integral with and extending from the upright support, the frame segment being couplable to the second horizontal support, where the horizontal support and the second horizontal support are configured to, in use, be spaced apart a sufficient distance to allow the frame segment to rotate 180 degrees about the horizontal axis.

6. The clearance check device of claim 4 configured such that the frame segment can be coupled to the horizontal support at different locations along the frame segment at different times.

7. The clearance check device of claim 1, further comprising a second upright support to which the frame segment may be coupled such that the frame segment is coupled to both, and spans a space between, the first and second upright supports.

8. A clearance check device configured to check for a potential collision between an object and a medical device component represented by the clearance check device and capable of orbiting at least partially about the object at a later time, the clearance check device comprising:
   an upright support;
   a horizontal support couplable to or integral with and extending from the upright support;
   a frame segment couplable to the horizontal support so as to rotate about a vertical axis that passes through the horizontal support; and
   a clearance member couplable to the frame segment.

9. The clearance check device of claim 8, where the frame segment is also releasably couplable to the upright support.

10. The clearance check device of claim 8, where the frame segment is releasably and rotatably couplable to the upright support, and releasably couplable to the horizontal support, such that the frame segment can be rotated about a horizontal axis that passes through the upright support.

11. The clearance check device of claim 10, further comprising a second horizontal support couplable to or integral with and extending from the upright support, the frame segment being couplable to the second horizontal support, where the horizontal support and the second horizontal support are configured to, in use, be spaced apart a sufficient distance to allow the frame segment to rotate 180 degrees about the horizontal axis.

12. The clearance check device of claim 8 configured such that the frame segment can be coupled to the horizontal support at different locations along the frame segment at different times.

13. The clearance check device of claim 8, where the clearance member comprises at least one of an arc segment and a disc segment.

14. The clearance check device of claim 8, further comprising a protractor couplable to the horizontal support and configured to measure the degree of rotation of the frame segment.

15. The clearance check device of claim 14, where the frame segment is configured to be coupled to the protractor at different degrees of rotation at different times.

16. The clearance check device of claim 8, where the position of the clearance member is configured to be adjustable along a length of the frame segment.

17. The clearance check device of claim 8, where the clearance member comprises a first end and a second end opposite the first end, where the first end comprises at least one of an arced frame segment and a disk segment and the clearance member is configured to couple to the frame segment at or near the second end.

18. A clearance check method comprising:
   positioning a patient on a table;

positioning a clearance check device comprising a frame segment adjacent the patient so that the frame segment substantially aligns with a transverse plane that passes through a treatment target in or on the patient; and testing for contact between the clearance check device and the patient or the table.

19. The method of claim 18, where positioning the patient on the table comprises aligning the patient with at least two in-room lasers that emit beams that are substantially perpendicular and positioning the clearance check device comprises aligning the clearance check device with the at least two in-room lasers.

20. The method of claim 19, where the clearance check device further comprises a clearance member that is selectively couplable to the frame segment such that a position of the clearance member is adjustable along a length of the frame segment and where testing for contact comprises positioning the clearance member on the frame segment at an angle that substantially corresponds to a gantry angle, rotating the frame segment about a vertical axis by an angle of rotation, and measuring the angle of rotation if contact between the patient and the clearance member is made or confirming that no contact between the patient and the clearance member is made at a couch angle.

* * * * *